US 6,744,498 B2

(12) United States Patent
Henze et al.

(10) Patent No.: US 6,744,498 B2
(45) Date of Patent: Jun. 1, 2004

(54) METHOD AND DEVICE FOR THE OPTICAL DETECTION OF FOREIGN FIBERS AND OTHER IMPURITIES IN A LONGITUDINALLY TRAVELING YARN

(75) Inventors: Herbert Henze, Mönchengladbach (DE); Olav Birlem, Schwalmtal (DE)

(73) Assignee: W. Schlafhorst AG & Co. (DE)

( * ) Notice: Subject to any disclaimer, the term of this patent is extended or adjusted under 35 U.S.C. 154(b) by 216 days.

(21) Appl. No.: 09/793,013

(22) Filed: Feb. 26, 2001

(65) Prior Publication Data

US 2001/0022656 A1 Sep. 20, 2001

(30) Foreign Application Priority Data

Feb. 26, 2000 (DE) .......................... 100 09 131

(51) Int. Cl.$^7$ .............................................. G01N 21/00
(52) U.S. Cl. ................... 356/238.3; 356/238.1; 356/238.2; 356/429; 356/430; 250/559.4; 250/559.41
(58) Field of Search ............... 356/238.2, 238.3, 356/430, 429, 238.1; 250/559.4, 559.41, 559.45

(56) References Cited

U.S. PATENT DOCUMENTS

| | | | | |
|---|---|---|---|---|
| 4,739,176 A | | 4/1988 | Allen et al. | ............... 250/572 |
| 5,178,008 A | * | 1/1993 | Aemmer | ................ 700/144 |
| 5,499,794 A | * | 3/1996 | Aeppli | ............... 250/559.41 |
| 5,654,554 A | * | 8/1997 | Feller et al. | ........... 250/559.45 |
| 6,175,408 B1 | * | 1/2001 | Henze et al. | ........... 356/238.3 |
| 6,380,548 B1 | * | 4/2002 | Henze et al. | ............ 250/559.4 |

FOREIGN PATENT DOCUMENTS

| | | |
|---|---|---|
| DE | 36 35 267 A1 | 5/1987 |
| DE | 297 19 245 U1 | 4/1998 |
| EP | 0 572 592 B1 | 6/1967 |
| EP | 0 399 945 B1 | 11/1990 |
| EP | 0 197 763 B1 | 9/1991 |
| EP | 0 652 432 | 5/1995 |
| EP | 0 761 585 A1 | 3/1997 |
| EP | 0 884 409 A1 | 12/1998 |
| EP | 0 553 446 B1 | 3/1999 |
| WO | WO 93/19359 | 9/1993 |
| WO | WO 95/29396 | 11/1995 |
| WO | WO 98/33061 | 7/1998 |

OTHER PUBLICATIONS

Melliand Textile Reports Mar. 1998; p. 129.
German Search Report .
European Search Report EP 01 10 0854.

* cited by examiner

Primary Examiner—Michael G. Lee
Assistant Examiner—Steven S. Paik
(74) Attorney, Agent, or Firm—Kennedy Covington Lobdell & Hickman, LLP

(57) ABSTRACT

Yarn impurities are detectable by a method and device wherein a first diameterdependent signal is obtained in a first measurement of a linearly traveling yarn, the intensity of the light for a second measurement is set as a function of the first signal to compensate for the effect of the yarn diameter on the light reflected by the yarn and then the second electrical signal can be directly evaluated for detecting yarn impurities. The invention improves the detection of impurities, for example in connection with spinning and bobbin winding machines.

19 Claims, 3 Drawing Sheets

METHOD AND DEVICE FOR THE OPTICAL DETECTION OF FOREIGN FIBERS AND OTHER IMPURITIES IN A LONGITUDINALLY TRAVELING YARN

CROSS-REFERENCES TO RELATED APPLICATIONS

This application claims the benefit of German patent application 10009131.8 filed Feb. 26, 2000, herein incorporated by reference

FIELD OF THE INVENTION

The present invention relates generally to a method and a device for the optical detection of impurities, in particular foreign fibers, in a longitudinally traveling yarn, and relates more particularly to such a method wherein light is emitted in the direction of the yarn, the intensity of the transmitted light is measured and converted into a first electrical signal whose value is a function of the instantaneous diameter of the yarn, the light reflected by the yarn is also measured, and a second electrical signal is produced.

BACKGROUND OF THE INVENTION

The detection of impurities is of great importance in the production of yarns. Impurities, particularly foreign fibers, can have disadvantageous effects on the final product.

It is known from European Patent Publications EP 0 197 763 and EP 0 553 545 to monitor a yarn in front of a background with the same reflecting ability as the yarn. Thus, it is intended that the amount of reflected light be essentially independent of the diameter of the yarn and a change in the reflected light does not indicate a change of the yarn diameter, but an impurity, for example as a result of foreign fibers. In this case, it is necessary to match the reflections from the background and the yarn very exactly to each other, because otherwise thick or thin places in the yarn cause changes in the reflected light and distort the results of the foreign fiber detection. The matching is elaborate, can only be automated to a limited extent or not at all, and moreover must be performed with every change in the fiber material, such as after a batch change, for example.

European Patent Publications EP 0 553 446 and EP 0 572 592 disclose methods and devices for detecting foreign fibers, wherein light from an illumination device is cast on the moving yarn, where it is reflected and transmitted. The reflected light and the transmitted light are each converted into electrical signals. These two electrical signals are linked to each other and a further electrical signal is thereby obtained, in which the foreign fibers are indicated and the other yarn defects, such as thick or thin places, are suppressed. With such signal linkages, the signals are customarily processed in the form of digital signals. Errors may occur in the value of a digital signal if rounding of the signal value is necessary in the course of converting analog signals into discrete digital signals which, in connection with the detection offoreign fibers, can lead to distortions of the measured results. In case of changes of the reflection signal, the signal portions which are dependent on the diameter can be ten, or even a hundred times, greater than the foreign fiber-dependent signal portions. Small errors during the linkage of the signals and the elimination of the diameter-dependent signal portions can lead to a considerable distortion of the smaller amount of the foreign fiber signal, and therefore of the results of the foreign fiber detection.

Another device is known from European Patent Publication EP 0 572 592, by means of which changes of the light from the light source, which are caused by dirt, are compensated by keeping the intensity of the light source constant. In this manner, it is intended to avoid changes in the light which develop over a long term or over a long time period, such as can be caused by dirt.

OBJECT AND SUMMARY OF THE INVENTION

It is accordingly an object of the present invention to reduce the disadvantages in connection with the known methods and devices for detection of foreign fibers, and to improve the detection of impurities in longitudinally traveling yarn.

The method of the present invention seeks to achieve this object by optically detecting foreign fibers and other impurities in a longitudinally traveling yarn, through the steps of emitting a light in the direction of the yarn; measuring the intensity of the emitted light; producing a first electrical signal based on the measuring of the emitted light intensity, the first signal being of a value which is a function of the instantaneous diameter of the yarn; following the formation of the first electrical signal, adjusting the intensity of the emitted light as a function of the yarn diameter based on the first electrical signal to compensate for the effect of the yarn diameter on the light reflected by the yarn; then measuring light reflected by the yarn; producing a second electrical signal based on the measuring of the reflected light; and directly using the second electrical signal for detecting impurities in the yarn. A matching of the reflecting capability of the measuring background with the reflecting capability of the yarn is no longer required for this method. Since in accordance with the invention signal portions which depend on the diameter are not even entered into the second signal, and changes in the second signal directly indicate impurities, it is possible to omit computing steps for linking the second signal with another signal, or with a signal which to a large degree is dependent on the diameter, thus eliminating the dependency on the diameter for detecting the foreign fiber proportion. Any rounding or computational errors caused by such computing steps, as well as the summation of such errors, is prevented.

The present invention further prevents rounding errors which occur in converting analog to digital signals in that the first electrical signal is generated in the form of an analog signal. A possible, but undesired, influencing of the measured values is prevented in a simple way by registering the first and second electrical signals at a predetermined clock frequency, or by pulsing the light source at a predetermined clock frequency.

Through the present manner of controlling the intensity of the emitted light in obtaining the second electrical signal, a completely different operating mechanism exists then in comparison to the device for regulating the output of the light source known from European Patent Publication EP 0 572 592. While the known device is intended to compensate for changes and to always maintain the light intensity constant, the control of the intensity of the emitted light in the present invention for forming the second electrical signal is purposely not kept constant, in contrast to the known device, but is set as a function of the first electrical signal, and therefore as a function of the yarn diameter. Thus, in accordance with the present invention, the light intensity of the light source for forming the second electrical signal is changed when a change of the first electrical signal occurs whereby, with an increased yarn diameter, the light intensity is set correspondingly lower, and with a decreased yarn diameter, the light intensity is set correspondingly higher.

The outlay for setting the intensity of the light source as a function of the first electrical signal can be reduced by setting a constant value of the light intensity of the light source in connection with the first measurement for forming the first signal. As a result, the diameter-dependent first measurement for forming the first signal always takes place under the same conditions, and the first signals can be directly used as a measurement of the instantaneous diameter of the yarn. The first electrical signal can be employed not only for controlling the intensity of a light source, but can additionally be evaluated for monitoring thick and thin places in the yarn.

In a preferred embodiment of the method, the second electrical signal is obtained at a time delay in respect to the first electrical signal at a measurement point which is located downstream in the direction of the yarn travel, with the time delay being controlled as a function of the yarn velocity such that both signals are obtained at the same location or section along the yarn. An extremely great measurement accuracy and measurement dependability is thereby assured.

The present invention also contemplates a novel device for performing the afore-described method and, particularly, is advantageous in compensating for changes in light intensity caused by aging or soiling of the light sources.

The second electrical signal obtained in accordance with the invention leads to increased measuring sensitivity in the course of the optical detection of impurities. Critical areas, such as the differentiation between dark brown and black, or the differentiation between off-white and pure white, can be easily controlled without problems through the present invention. The invention permits a clear improvement in the detection of impurities, in particular foreign fibers, in linearly moved yarn.

Further advantageous embodiments of the invention will be understood from the following disclosure of exemplary embodiments of the invention represented in the drawings.

DETAILED DESCRIPTION OF THE PREFERRED EMBODIMENTS

Figure 1:
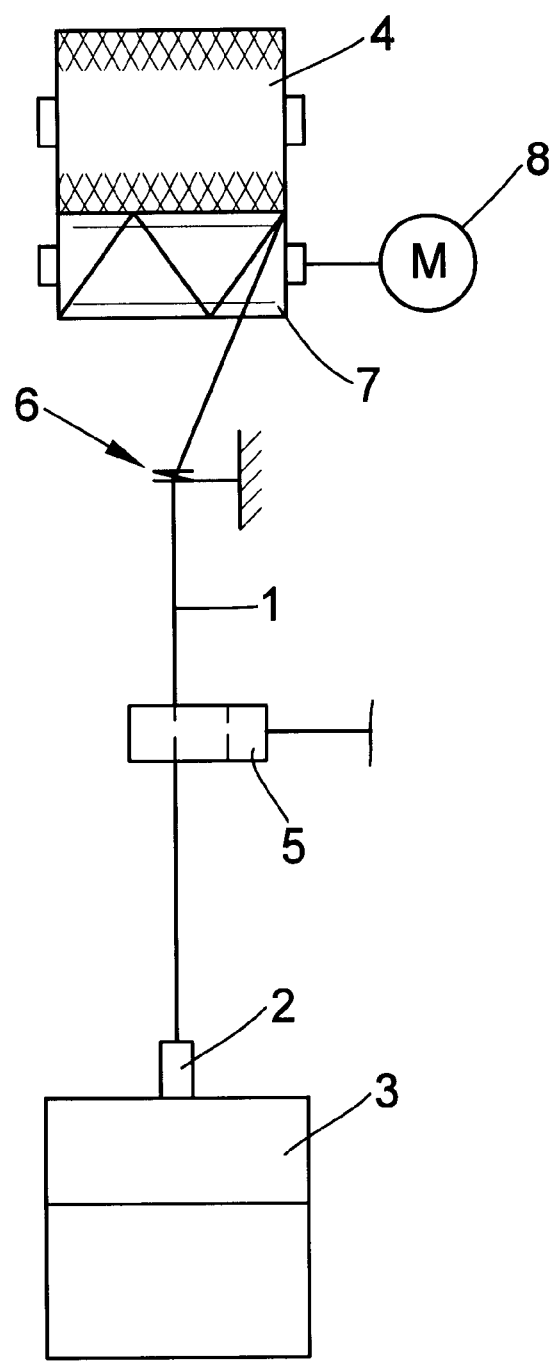
FIG. 1 is a schematic representation of a bobbin winding station in accordance with the present invention.

In the bobbin winding station represented in FIG. 1, a yarn 1 is drawn out of a spinning box 3 through a small draw-off tube 2 and is wound on a cheese 4. Between the small draw-off tube 2 and the cheese 4, the yarn 1 passes through a cleaning device 5 and a guide eye 6. A drive drum 7 drives the cheese 4 by means of surface frictional contact during the winding process. Rotary movement is imparted to the drive drum 7 by a motor 8. The cleaning device 5 is used for monitoring the quality of the running yarn 1. The cleaning device 5 includes an integrated measuring station. The cleaning device 5 is connected with further devices for the control, data storage or data evaluation, and the triggering of further elements of the bobbin winding station, or of the spinning machine.

Figure 2:
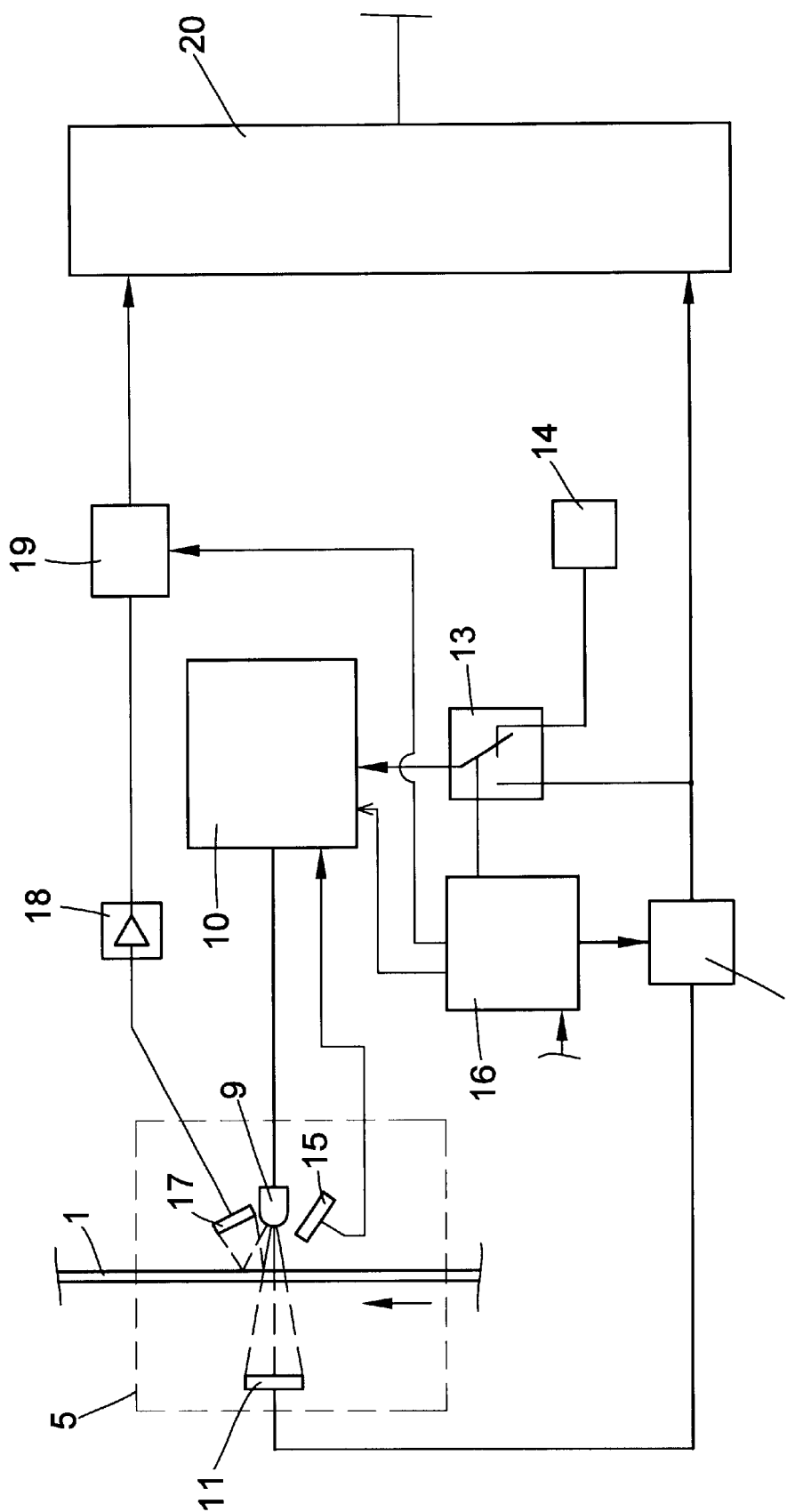
FIG. 2 is a schematic representation of a detection device at the bobbin winding station of FIG. 1, in accordance with the present invention.

A detection device is represented in simplified form in FIG. 2, and includes the cleaning device 5 which has a light source 9 and a first control device 10. The light source 9 emits light in the direction toward the yarn 1 and, in a known manner, provides an image of the yarn 1 on a sensor 11. In a first measuring phase, the sensor 11 performs a first measurement and forms a signal which is representative of the instantaneous yarn diameter and is converted into an analog electrical signal. This signal is supplied to the memory 12 of a memory device and is stored therein. In this first phase, a first control device 10 receives a signal of constant value coming from a data memory 14 via a change-over switch 13. This switching position is represented in FIG. 2. The signal from the data memory 14 is used as a control signal for setting the intensity of the light emitted by the light source 9 in this first measuring phase. Light emitted by the light source 9 is detected by a sensor 15 positioned such that this detected light is not affected by the yarn 1. The sensor 15 is a part of a control device, known per se, by means of which the effects of soiling or aging of the light source are eliminated and which causes the intensity of the light emitted by the light source 9 in the first measuring phase to be maintained constant.

The length of this first measuring phase is controlled by a second control device 16. The second control device 16 is connected with the memory 12, with the first control device 10, and with the change-over switch 13 and further elements of the winding station. The second control device 16 terminates the first measuring phase by actuating a switching of the change-over switch 13. By means of the actuation of the change-over switch 13, the first control device 10 also receives the control signal coming from the memory 12, whereby a second measuring phase starts. This analog electrical signal from the memory 12 represents the instantaneous diameter of the yarn 1 in the first measuring phase. As a function of this signal, the first control device 10 now sets the intensity of the light source 9 to compensate for the effect of the yarn diameter on the light reflected by the yarn. Light reflected by the yarn 1 is detected by a sensor 17 and a second electrical signal is formed, which is supplied via an amplifier 18 to a memory 19. The second electrical signal is forwarded from the memory 19 to an evaluation device 20, and is directly evaluated for detecting impurities. If a change occurs in the reflected light, and therefore correspondingly changes the second signal, the change represents a yarn impurity.

At the presence of the second electrical signal, the second control device 16 terminates the second measuring phase by actuating a reverse switching of the change-over switch 13, so as to again provide the first control device 10 with the signal from the data memory 14. In this manner, the two-phase measuring cycle starts again at the beginning. The clock frequency of the measuring cycles is controlled by the second control device 16 and preferably lies in the kilocycle range. The measurements follow each other so rapidly as to be equivalent to a continuous measurement. The light source 9 is switched off when the change-over switch 13 is actuated, and is switched on again immediately following the change-over process.

Figure 3:
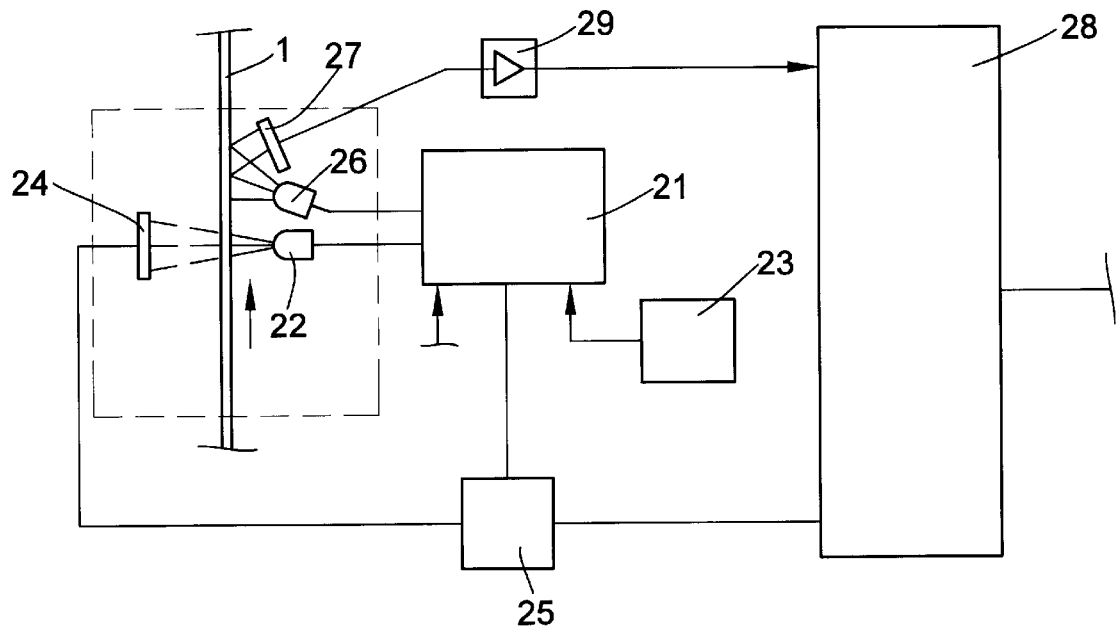
FIGS. 3 and 4 are schematic representations of further exemplary embodiments of detection devices in accordance with the present invention.

An alternative exemplary embodiment of the detection device is represented in FIG. 3. A light source 22 is controlled by a control device 21. The control device 21 is connected with a data memory 23 and is provided therefrom with a control signal for setting the intensity of the light emitted by the light source 22. This control signal is maintained constant. A control circuit can be provided in a further alternative embodiment, which compensates for aging and soiling of the light source 22 in a known manner.

The light emitted by the light source 22 provides an image of the yarn 1 on the sensor 24. The sensor 24 forms a signal which represents the instantaneous diameter of the yarn 1 and which is supplied as a first analog electrical signal to a memory 25. The control device 21 is provided with this signal from the memory 25 for controlling a second light source 26. The intensity of the light source 26 is set by means of this signal from the memory 25 to compensate for the effect of the yarn diameter on the light reflected by the yarn. Measurement of the reflected light takes place by means of the sensor 27.

The sensor 27 forms a second electrical signal from this second measurement, which is supplied via an amplifier 29 to an evaluation unit 28 wherein the measuring of the second electrical signal is performed with a time delay compared with the measurement of the first electrical signal. The time delay is controlled such that both measurements take place at two spaced apart measurement points, but at the same point, or the same section, along the yarn 1. To be able to match the time delay to the yarn velocity, the control device is connected with devices for detecting the yarn velocity and receives signals from these devices, not shown for reasons of simplicity, which represent the instantaneous yarn velocity.

The second electrical signal is directly used in an evaluation unit 28 for detecting yarn impurities. The measuring and control processes run continuously. It is alternatively possible to perform the clocking of measuring phases within the measuring cycles. Besides the detection of yarn impurities, additional quality monitoring takes place by means of evaluating the first electrical signal respectively transmitted from the memory 25 to the evaluation device 28.

Figure 4:
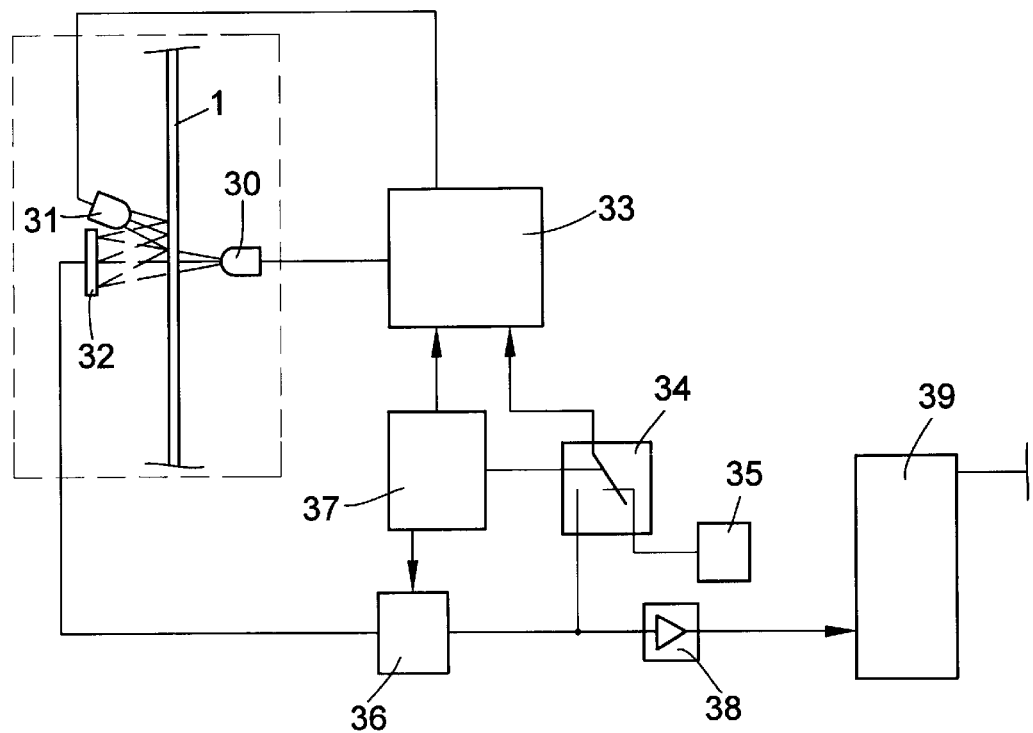

In a further alternative exemplary embodiment of the device represented in FIG. 4, the light emitted by two light sources 30, 31 is measured by a single sensor 32. In a first measuring phase, a control device 33 is provided with a control signal, which is maintained constant, from a data memory 35 via a change-over device 34. This switching position of the change-over device 34 is represented in FIG. 4. In the first measuring phase, the light source 30 is switched on by the control device 33, and its intensity is set to a value which is a function of the control signal from the data memory 35 such that an equal intensity occurs in every first measuring phase. The light emitted by the light source 30 provides an image of the yarn 1 on the sensor 32. The sensor 32 forms a first signal from the detected light, which represents the diameter of the yarn 1. This signal is provided as an analog electrical signal to a memory 36 and is stored therein. The control device terminates the first measuring phase by switching off the light source 30. The clock frequency of switching on and off the light source 30 is predetermined in the control device 33 by the control device 37, which is connected with the latter.

Then, the control device 37 actuates the change-over device 34 after which the control device 33 is provided with the first electrical signal from the memory 36. The light source 31 is switched on by the control device 33, and its intensity in this second measuring phase is set as a function of the first electrical signal to compensate for the effect of the yarn diameter on the light reflected by the yarn.

Light reflected by the yarn 1 in the second measuring phase is measured by the sensor 32 and a second signal is formed, which is provided to the memory 36 in the form of an electrical signal. The first electrical signal, as well as the second electrical signal, are transmitted from the memory 36 via an amplifier 38 to the evaluation device 39. Subsequently the light source 31 is switched off again by the control device 33. The control device 37 actuates the change-over device 34 and therewith terminates the second measuring phase, and thus the entire first measuring cycle.

Following the actuation of the change-over device 34, the control device 33 is again provided with the signal from the data memory 35, and the second measuring cycle starts. The second measurement is performed with a time delay in respect to the first measurement such that the second measurement takes place at the same location along the yarn as the first measurement. The time delay is adapted in a manner known per se to the instantaneous yarn velocity.

Alternatively to these exemplary embodiments, the control and memory elements can be arranged in a single microprocessor, or in any other arrangement inside or outside of the measuring station.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method for optical detection of foreign fibers and other impurities in a longitudinally traveling yarn, comprising the steps of:

emitting a light in the direction of the yarn;

measuring the intensity of the emitted light;

producing a first electrical signal based on the measuring of the emitted light intensity, the first signal being of a value which is a function of the instantaneous diameter of the yarn;

following the formation of the first electrical signal, adjusting the intensity of the emitted light as a function of the yarn diameter based on the first electrical signal to compensate for the effect of the yarn diameter on the light reflected by the yarn;

then measuring light reflected by the yarn;

producing a second electrical signal based on the measuring of the reflected light; and directly using the second electrical signal for detecting impurities in the yarn.

2. The method in accordance with claim 1, wherein the producing of the first electrical signal comprises generating an arialog electrical signal as the first electrical signal.

3. The method in accordance with claim 1, further comprising detecting the first and second electrical signals at a predetermined clock frequency.

4. The method in accordance with claim 1, further comprising pulsing the emitted light at a predetermined clock frequency.

5. The method in accordance with claim 1, wherein during the first measurement and producing of the first signal, the emitting of the light is maintained at a constant value of light intensity.

6. The method in accordance with claim 1, wherein the producing of the second electrical signal is performed after a time delay in respect to the first electrical signal and at a measuring point located downstream along the traveling direction of the yarn in respect to the measuring the first electrical signal, the time delay being a function of the yarn velocity such that both signals are obtained at the same location along the yarn.

7. A device for optical detection of foreign fibers and other impurities in a longitudinally traveling yarn, comprising:

an illumination device for emitting light in the direction toward the yarn;

a sensor arrangement for measuring light, for performing a first measurement of the light emitted from the illumination device and producing therefrom a first electrical signal of a value which is a function of the instantaneous diameter of the yarn, and for performing a second measurement of the light reflected by the yarn and producing therefrom a second electrical signal from the reflected light;

a first control device for controlling the illuminating device, the first control device comprising means operative in response to the first electrical signal for adjusting the intensity of the light emitted by the illuminating device as a function of the yarn diameter based on the first electrical signal to compensate for the effect of the yarn diameter on the light reflected by the yarn; and an evaluation device for directly evaluating the second electrical signal for detecting impurities in the yarn.

8. The device in accordance with claim 7, wherein the illuminating device comprises two light sources including a first light source which only emits light for the first measurement, and a second light source which only emits light for the second measurement.

9. The device in accordance with one of claims 7, wherein the sensor arrangement has two sensors including a first sensor which only detects light in the course of the first measurement and a second sensor which only detects reflected light in the course of the second measurement.

10. The device in accordance with claim 9, wherein the second sensor is arranged remotely from the first sensor downstream of the first sensor in the traveling direction of the yarn.

11. The device in accordance with claim 7, further comprising a second control device for controlling further processing of the first and second signals from the first and second measurements as a function of a frequency thereof.

12. The device in accordance with claim 7, further comprising a memory device with at least one memory for storing the first signal, the memory device being connected with a second control device.

13. The device in accordance with claim 7, further comprising a change-over device for receiving a control signal from a data memory or a control signal from a memory which stores the first signal, for controlling the intensity of the light source.

14. A method for optical detection of foreign fibers and other impurities in a longitudinally traveling yarn, comprising the steps of:

emitting light of a first intensity in the direction of the yarn;

measuring the diameter of the yarn;

generating a first electrical signal whose value is indicative of the measured yarn diameter;

after generating the first electrical signal, emitting light of a second intensity in the direction of the yarn, wherein the difference between the second intensity and the first intensity is a function of the diameter of the yarn;

while emitting light of the second intensity, measuring the light reflected by the yarn;

generating a second electrical signal whose value is indicative of the measured reflected light; and detecting impurities in the yarn on the basis of the value of the second electrical signal.

15. The method in accordance with claim 14, wherein the step of generating a first electrical signal comprises generating an analog electrical signal.

16. The method in accordance with claim 14, further comprising the step of detecting the first and second electrical signals at a predetermined clock frequency.

17. The method in accordance with claim 14, further comprising the step of pulsing the emitted light at a predetermined clock frequency.

18. The method in accordance with claim 14, wherein the method is carried out repeatedly, and wherein during each repeated step of measuring the diameter of the yarn, the first intensity of emitted light is maintained at a constant value.

19. The method in accordance with claim 14, wherein the step of measuring the yarn diameter is performed at a first measuring point, wherein the step of generating the second electrical signal is performed after a time delay with respect to the first electrical signal, wherein the step of measuring the light reflected by the yarn is performed at a second measuring point located downstream along the traveling direction of the yarn with respect to the first measurement point, and wherein the time delay is a function of the yarn velocity such that both signals are obtained relative to the same portion of the yarn.

* * * * *